(12) United States Patent
Shen

(10) Patent No.: US 11,793,541 B2
(45) Date of Patent: Oct. 24, 2023

(54) PLAQUE REMOVAL DEVICE

(71) Applicant: Shanghai Sixth People's Hospital, Shanghai (CN)

(72) Inventor: Chengxing Shen, Shanghai (CN)

(73) Assignee: Shanghai Sixth People's Hospital, Shanghai (CN)

( * ) Notice: Subject to any disclaimer, the term of this patent is extended or adjusted under 35 U.S.C. 154(b) by 192 days.

(21) Appl. No.: 17/240,693

(22) Filed: Apr. 26, 2021

(65) Prior Publication Data

US 2022/0226015 A1 Jul. 21, 2022

(30) Foreign Application Priority Data

Jan. 15, 2021 (CN) .............................. 202110056375

(51) Int. Cl.
*A61B 17/3207* (2006.01)
*A61B 17/00* (2006.01)

(52) U.S. Cl.
CPC .............. *A61B 17/320725* (2013.01); *A61B 2017/00292* (2013.01); *A61B 2017/00526* (2013.01); *A61B 2017/00862* (2013.01); *A61B 2017/00867* (2013.01)

(58) Field of Classification Search
CPC .. A61B 17/320725; A61B 2017/22061; A61B 2017/22001; A61B 2017/320733; A61B 2017/32075; A61B 2017/00292; A61B 2017/00862

See application file for complete search history.

(56) References Cited

U.S. PATENT DOCUMENTS

| | | | | |
|---|---|---|---|---|
| 6,355,051 | B1 * | 3/2002 | Sisskind | A61F 2/0108 606/200 |
| 2002/0173817 | A1 * | 11/2002 | Kletschka | A61M 25/1011 606/192 |
| 2011/0184456 | A1 * | 7/2011 | Grandfield | A61B 17/320725 606/200 |
| 2018/0116689 | A1 * | 5/2018 | Nakano | A61B 17/221 |
| 2020/0121332 | A1 * | 4/2020 | Nakagawa | A61B 17/221 |
| 2020/0121355 | A1 * | 4/2020 | Eskridge | A61B 17/320725 |
| 2020/0146852 | A1 * | 5/2020 | Raychev | A61F 2/88 |
| 2020/0316338 | A1 * | 10/2020 | Spivey | A61M 5/31596 |

* cited by examiner

*Primary Examiner* — Timothy J Neal
*Assistant Examiner* — James R McGinnity
(74) *Attorney, Agent, or Firm* — Clement Cheng

(57) ABSTRACT

The invention discloses a plague removal device, comprising, a push catheter, a plaque scraping stent, a support tube, an elastic filter membrane, a guide catheter, and a handle, wherein the plaque scraping stent is a mesh structure sleeved outside the support tube, a distal end of the plaque scraping stent is fixed on a distal end of the support tube, a proximal end of the plaque scraping stent is fixed on a distal end of the push catheter, the support tube is sleeved inside the push catheter; a distance between the distal end of the push catheter and the distal end of the support tube is adjusted by the handle, so that an outer diameter of the plaque scraping stent is varied. The unique structure design of "tapered structure" in the present invention can ensure good compliance during the entry and withdrawal of the stent.

7 Claims, 4 Drawing Sheets

PLAQUE REMOVAL DEVICE

BACKGROUND OF THE INVENTION

1. Field of the Invention

The invention relates to the technical field of medical devices, and more particularly, to a plaque removal device.

2. Description of the Related Art

Atherosclerosis is a systemic and progressive disease of the whole body. Atherosclerotic plaques mainly build up inside the intima of the arteries. When the atherosclerotic plaques continue to build up and have a large volume, they may impede the blood flow inside blood vessels, which may lead to a result that tissues in an area which is innervated by those blood vessels, may suffer from ischemic symptoms. In the meantime, it may contribute to the rupture of the atherosclerotic plaques. The necrotic materials inside the ruptured plaques will release a large amount of tissue factor (known as TF). TF is the strongest substance responsible for initiation of platelet aggregation and it may lead to the formation of thrombus. And the worst consequence is that the whole blood vessel is fully clogged or partially clogged. When the blood vessel is fully clogged or partially clogged, clinical manifestations vary slightly from one organ to another organ. For example. Main symptoms for cardiac ischemia is angina pectoris or myocardial infarction; if blood is clogged in cerebral vessels, symptoms may include insufficiency of cerebral blood supply, cerebral infarction or even cerebral hemorrhage; if blood is clogged in arteries of lower extremities, symptoms may include severe pain or intermittent claudication. One of the most effective ways to treat this type of disease is to restore the blood flow blocked by the plaques or thrombus. Such a method can not only reduce or eliminate symptoms, but also improve the long-term prognosis.

Now, in addition to drug therapy, two invasive methods are available for plaque removal, wherein one is arterial plaque atherectomy and the other is high-speed rotational atherectomy.

These two methods mainly use rotary cutting devices and rotary atherectomy devices to cut or grind the coronary atherosclerotic plaque tissue from the blood vessel wall, and the coronary atherosclerotic plaque tissue is then discharged out of the body through a catheter. However, atherectomy has some disadvantages, for example, normal body parts may be removed by atherectomy, or coronary arteries may be cut by atherectomy, thus, it is not suitable for treatment is thin or curved, calcified blood vessels. Moreover, expensive atherectomy devices are needed for carrying out the atherectomy; higher and complex requirements are imposed on the operation of the atherectomy; and excessive complications may incur, all of those problems limit its clinical applications. While the high-speed rotational atherectomy and coronary arteryinternal rotational atherectomy are mainly used for treatment of highly calcified lesions. Precision devices are needed for the high-speed rotational atherectomy and coronary arteryinternal rotational atherectomy, and surgeons should have excellent skills. Thus, the method is not suitable for the treatment of ordinary lesions.

In conclusion, there exists a need for providing a method for solving the problem that in-situ plagues lesions in the vascular lumen are difficult to remove, and the method can be configured to remove new plaques or hyperplastic intima in the stent. Of note, people focus on providing a method which is low in cost, which is effective, and is simple to operate.

SUMMARY OF THE INVENTION

Given that the foregoing problems exist in the prior art, the present invention provides a plague removal device. By using the plague removal device, the problem of in-situ plagues lesions in the vascular lumen being difficult to remove is solved. In addition, the plague removal device can be applied to the removal of new plaques or hyperplastic intima in the stent.

For the above-mentioned objects, the invention adopts the following technical solutions:

The invention provides a plague removal device, comprising, a push catheter, a plaque scraping stent, a support tube, an elastic filter membrane, a guide catheter, and a handle, wherein the plaque scraping stent is a mesh structure sleeved outside the support tube, a distal end of the plaque scraping stent is fixed on a distal end of the support tube, a proximal end of the plaque scraping stent is fixed on a distal end of the push catheter, the support tube is sleeved inside the push catheter; a distance between the distal end of the push catheter and the distal end of the support tube is adjusted by the handle, so as to control an outer diameter of the plaque scraping stent to be varied.

The objects of the invention can also be achieved by using the following technical solutions:

Preferably, the plaque removal device comprises a proximal stent, a lumbar stent and a distal stent; wherein the proximal stent and the distal stent have a conical net structure, each of the proximal stent and the distal stent comprises 3-6 wide support rods, wherein the wide support rods are distributed in a central symmetry manner, two thin support rods extend from the wide support rods, 12-24 connection points are formed at junctions of the thin support rods and the lumbar stent; the lumbar stent has a tubular net structure, and comprises 12-24 diamond-shaped lumbar grids.

Furthermore, when the distance between the distal end of the push catheter and the distal end of the support tube is less than a farthest distance, that is, when the plaque scraping stent is in an expanded state, an angle between two adjacent wide support rods is a first opening angle $\angle 1$, wherein the first opening angle is in a range of 5° to 20°; an angle between two adjacent thin support rods is a second opening angle $\angle 2$, wherein the second opening angle is in a range of 20° to 50°; an angle of the lumbar grids is a third opening angle $\angle 3$, wherein the third opening angle is in a range of 20° to 50°.

Furthermore, when the plaque removal device in the expanded state, the lumbar stent has an outer diameter of 2.0 mm to 3.5 mm.

Preferably, the proximal end of the plaque scraping stent is connected to the push catheter by pins or screws, and the distal end of the plaque scraping stent is welded, bonded or riveted to the distal end of the support tube.

Preferably, the plaque scraping stent is an integral part which is curved from a nitinol tube, wherein the nitinol tube has an outer diameter of 1.4 mm.

Preferably, a surface of the plaque scraping stent is provided with sharp edges for providing effective cutting.

Preferably, the elastic filter membrane covers an inner wall of the distal stent, and is fixed by stitching, bonding or welding.

Preferably, the elastic filter membrane is made of PET or ePTFE material, or the elastic filter membrane is formed by cross weaving or sinusoidal weaving, wherein the elastic filter membrane has a mesh size of 50 µm to 250 µm, and has a thickness of 10 µm to 200 µm.

Preferably, the handle comprises a luer taper, a safety lock, a slider device, a spring pressing cover, a screw and an upper and lower front handle.

Preferably, an inner surface of the upper and lower front handle is bonded to the proximal end of the guide catheter;

the proximal end of the support tube passes through the guide catheter and is fixedly connected to an inner surface of the screw; the slider device is in thread connection with an outer surface of the screw, the slider device is rotated to drive the screw to move axially, and thus to drive the support tube, the plaque scraping stent and the push catheter to move axially;

the proximal end of the push catheter passes through the guide catheter into the handle, so as to be contact with a distal end of the screw; when the plaque scraping stent moves to the farthest end, the proximal end of the push catheter is in fixed coordination with the spring pressing cover to push the spring pressing cover, the push catheter moves axially with respect to the support tube, to change the outer diameter of the plaque scraping stent.

Preferably, the spring pressing cover is marked with scales, and the outer diameter of the plaque scraping stent matches the reading shown on the spring pressing cover.

By adopting the above-mentioned technical solutions, the present invention has the following beneficial effects when compared with the prior art.

1. The unique structure design of "tapered structure" in the present invention can ensure good compliance during the entry and withdrawal of the stent. Moreover, the outer diameter of the stent can be precisely controlled to ensure the support of the stent by manipulating the handle. The specially designed grid unit in the middle of the plaque scraping stent can effectively scrape the subintimal plaque without damaging the normal vascular intima.

2. The distal end of the stent is provided with a filter membrane, so that the removed plaques can be fully recycled for repeated scraping.

3. The present invention is convenient to operate and can be accurately controlled, which greatly reduces the requirements on the operator's ability to operate the device.

4. The invention is simple in structure, which greatly reduces the costs for the device.

5. According to statistics, the number of percutaneous coronary interventions in China in 2018 was 915,256, and an average of 1.46 stents were implanted. The number of stents in 2018 was estimated to be about 1.33 million. The number of percutaneous coronary interventions (PCI) has increased by 21.5% when compared with that in 2017. In 2020, The number of percutaneous coronary interventions was more than 1 million. If 20% of lesions can be treated by removing plaques without implanting metal stents, more than 200,000 patients with this type of disease can be treated by using this method, which eliminates the need for the implantation of the stent. Therefore, it has a great prospect in terms of clinical application.

THE REFERENCE NUMERALS LIST

1—push catheter
2—plaque scraping stent
3—support tube
4—elastic filter membrane
5—guide catheter
6—handle
21—proximal stent
211—wide support rod
212—thin support rod
22—lumbar stent
23—distal stent
61—luer taper
62—safety lock
63—slider device
64—spring pressing cover
65—screw
66—upper and lower front handle
∠1 first opening angle
∠2 second opening angle
∠3 third opening angle

DETAILED DESCRIPTION

The present invention will now be described more fully hereinafter with reference to the accompanying drawings, in which exemplary embodiments of the invention are shown. However, this invention should not be construed as limited to the embodiments set forth herein. In this context of the invention, "proximal end" denotes an end closer to the operator, and "distal end" denotes an end away from the operator.

Example 1

Figure 1:
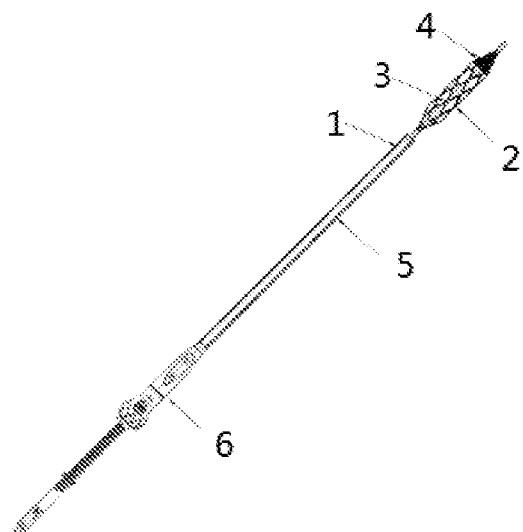
FIG. 1 is a schematic diagram of a plaque removal device according to the present invention.

As shown in FIG. 1, this embodiment provides a plaque removal device, comprising: a push catheter 1, a plaque scraping stent 2, a support tube 3, an elastic filter membrane 4, a guide catheter 5, and a handle 6.

Figure 2:
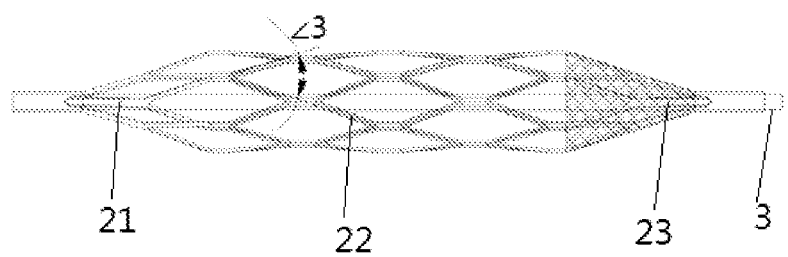
FIG. 2 is a front view of a plaque scraping stent according to the present invention when in the expanded state.
Figure 3:
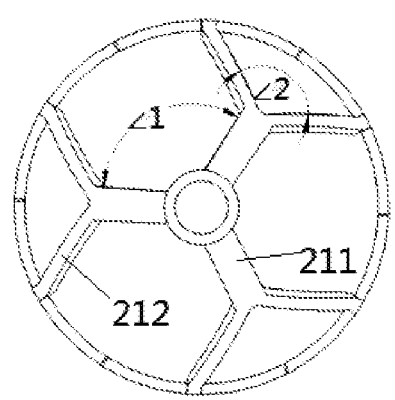
FIG. 3 is a side view of a plaque scraping stent according to the present invention when in the expanded state.

In particular, as shown in FIGS. 2-3, the plaque removal device 2 comprises a proximal stent 21, a lumbar stent 22 and a distal stent 23; wherein the proximal stent 21 and the distal stent 23 have a conical net structure, each of the proximal stent 21 and the distal stent 23 comprises 3 wide support rods 211, wherein the wide support rods 211 are distributed in a central symmetry manner, two thin support rods 212 extend from the wide support rods 211, 12 connection points are formed at junctions of the thin support rods 212 and the lumbar stent 22; the lumbar stent 22 has a tubular net structure, and comprises 12 diamond-shaped lumbar grids. FIG. 2 shows a first opening angle ∠1, a second opening angle ∠2 and a third opening angle ∠3. When the plaque scraping stent (2) changes from a collapsed state to an expanded state, the first opening angle ∠1 is in a range of 5° to 20°, the second opening angle ∠2 is in a range of 20° to 50°, and the third opening angle ∠3 is in a range of 20° to 50°. After the grid cell of the lumbar stent 22 is treated by physical and chemical methods, the surface of the stent is provided with sharp edges for effectively scraping subintimal plaques without damaging the normal vascular intima.

In addition, the angles of the first opening angle ∠1, the second opening angle ∠2 and the third opening angle ∠3 can be changed by the dimensions of a heat setting mold. In particular, the stent is fixed on the heat setting mold, and the mold is put into an experimental chamber type air circulation resistance furnace for heat treatment.

In this embodiment, the plaque scraping stent 2 is a mesh structure sleeved outside the support tube 3, a distal end of the plaque scraping stent 2 is fixed on a distal end of the support tube 3, a proximal end of the plaque scraping stent 2 is fixed on a distal end of the push catheter 1, the support tube 3 is sleeved inside the push catheter 1; a distance between the distal end of the push catheter 1 and the distal end of the support tube 3 is adjusted by the handle 6, so as to control an outer diameter of the plaque scraping stent 2 to be varied.

In particular, the proximal end of the support tube 3 passes through the guide catheter 5 and is fixedly connected to an inner surface of the screw 65; the slider device 63 is in thread connection with an outer surface of the screw 65, the slider device 63 is rotated to drive the screw 65 to move axially, and thus to drive the support tube 3, the plaque scraping stent 2 and the push catheter 1 to move axially;

the proximal end of the push catheter 1 passes through the guide catheter 5 into the handle 6, so as to be contact with a distal end of the screw 65; when the plaque scraping stent 2 is exactly located outside the guide catheter 5, the proximal end of the push catheter 1 is detachably connected with the spring pressing cover 64 through a matching configuration to push the spring pressing cover 64 towards the distal end; the push catheter 1 moves axially toward the distal end with respect to the support tube 3, so that the plaque scraping stent 2 is gradually expanded to a target outer diameter; when it is desired to retract the plaque scraping stent 2, the spring pressing cover 64 is pushed toward the proximal end until it reaches the nearest end; when the plaque scraping stent 2 gradually retracts to the original state, the matching configuration of the proximal end of the push catheter 1 and the spring pressing cover 64 is released.

The unique structure design of "conical gradient" in the present invention can ensure good compliance during the entry and withdrawal of the stent. Moreover, the outer diameter of the stent can be precisely controlled to ensure the support of the plaque scraping stent 2 by manipulating the handle.

Figure 4:
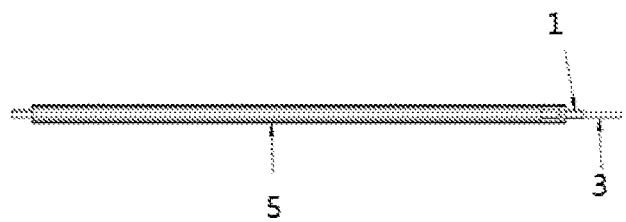
FIG. 4 is a diagram showing a matching configuration of a support tube, a push catheter, and a guide catheter according to the present invention.
Figure 5:
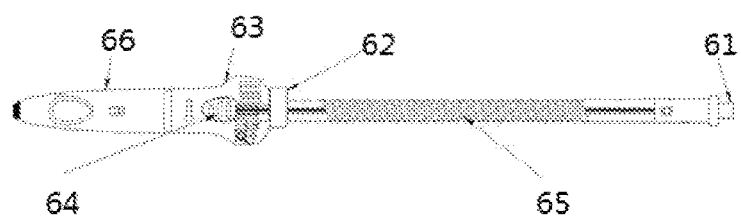
FIG. 5 is a schematic diagram of a handle according to the present invention.

In particular, as shown in FIG. 4, the support tube 3, the push catheter 1 and the guide tube 5 are successively sleeved from inside to outside; as shown in FIG. 5, the handle 6 comprises a luer taper 61, a safety lock 62, a slider device 63, a spring pressing cover 64, a screw 65 and an upper and lower front handle 66.

In a preferred embodiment, the handle 6 is further equipped with a safety lock 62, which acts as a limiter and can prevent the slider device 63 from sliding. Thus, the safety lock 62 is safe and effective.

In a specific embodiment, the push catheter 1 is made of metal, non-metal or metal-non-metal composite tube with good flexibility and strong support. The guide catheter 5 is composed of a three-layer structure, wherein the inner layer of the three-layer structure is made of polytetrafluoroethylene (PTFE) material; the middle layer is made of SS304 by braiding and winding process; and the outer layer is made of PEBAX.

Example 2

Steps for using the plague removal device provided in the present invention are as follows:

When in the initial state, the support tube 3 and the push catheter 1 are both in the guide catheter 5, and the plaque scraping stent 2 is in an unexpanded state.

Figure 6:
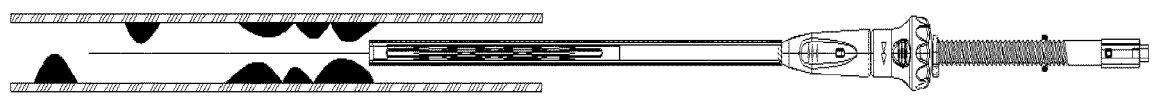
FIG. 6 is a schematic diagram showing a state where the plague removal device approaches a plaque in the vascular lumen along a micro guidewire according to the present invention.
Figure 7:
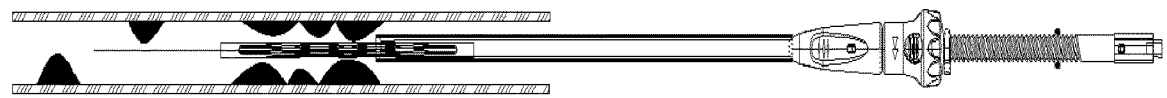
FIG. 7 is a schematic diagram showing a state where the plague scraping stent approaches the plaque along the guide catheter according to the present invention.
Figure 8:
FIG. 8 is a schematic diagram showing a state where the plaque scraping stent in the expanded state in the plaque removal device is positioned at the plaque according to the present invention.

Step S1: as shown in FIG. 6, insert a working cannula and the micro guidewire at a predetermined surgical position, the proximal self-supporting tube 3 of the micro guidewire passes through the luer taper 61 and out of the luer taper 61, and the distal end of the plaque removal device approaches a plaque in the vascular lumen along a micro guidewire;

Step S2: as shown in FIG. 7, as the slider device 63 is continuously rotated forward, the screw 65 is driven to move toward the distal end, and thus to drive the support tube 3, the plaque scraping stent 2 and the push catheter 1 to move toward the distal end until the plaque scraping stent 2 is fully exposed from the guide catheter 5 and is located at the plague;

Step S3: as shown in FIG. 8, the proximal end of the push catheter 1 is matched and fixed with the spring pressing cover 64, the spring pressing cover 64 is pushed toward the distal end, and the push catheter 1 moves axially toward the distal end with respect to the support tube 3, so that the plaque scraping stent 2 is gradually expanded until the spring pressing cover 64 is pushed to an ideal position, at this time the reading of the spring pressing cover 64 is consistent with the outer diameter of the plaque scraping stent 2;

Step S4: it is needed to push, pull, and rotate the handle 6 to change the position of the plaque scraping stent 2 for cutting the plaque, so that the plaque can be gradually ruptured;

Step S5: after the plaque is fully ruptured, pull the handle 6 toward the proximal end to make the plaque scraping stent 2 move toward the proximal end, and the fragments of the plaque are collected onto the elastic filter membrane 4;

Step S6: the spring pressing cover 64 is pushed toward the proximal end, and the push catheter 1 moves axially toward the proximal end with respect to the support tube 3, so that the plaque scraping stent 2 gradually retracts until the spring pressing cover 64 is pushed to the most proximal position, and the matching connection of the spring pressing cover 64 and the push catheter 1 is released. as the slider device 63 is continuously rotated in a reverse way, the screw 65 is driven to move toward the proximal end, and thus to drive the support tube 3, the plaque scraping stent 2 and the push catheter 1 to move toward the proximal end until the plaque scraping stent 2 fully retracts the guide catheter 5, and the plaque removal device is taken out of the working sleeve.

Example 3

Figure 9:
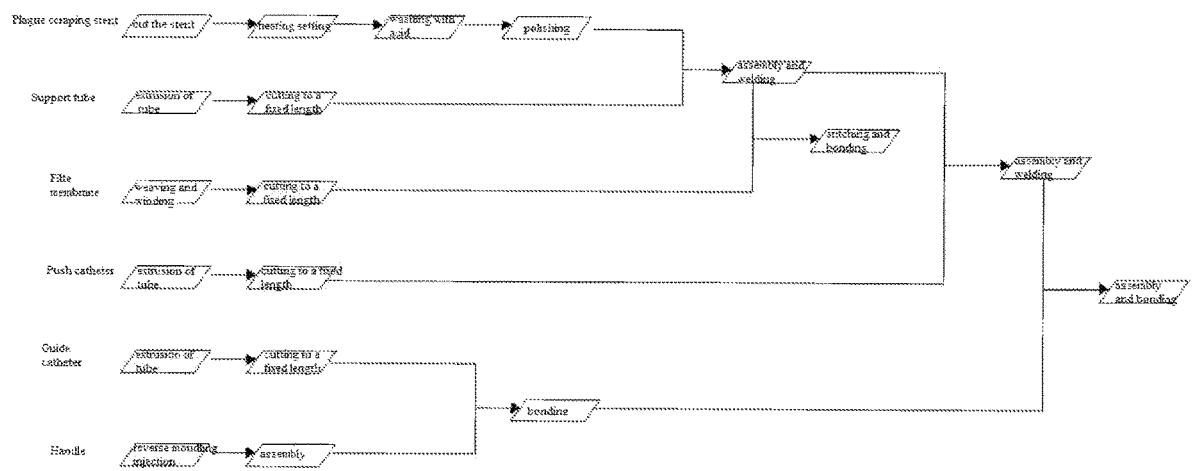
FIG. 9 is a flowchart showing a method for preparing the plaque removal device according to the present invention.

The embodiment provides a method for preparing the plague removal device in the example 1. As shown in FIG. 9, the method comprises the steps of:

Step A1. preparation of plaque scraping stent 2: a predetermined shape is cut from a nitinol tube by using a cutting machine to obtain a stent blank, heat treatment process is carried out in a box-type air circulation resistance furnace, the stent blank is expanded, residue on the inner and outer surfaces of the stent are treated with acid, then the inner and outer surfaces of the stent are polished by using an electrochemical polishing machine to make the stent smoother and sharper;

Step A2. preparation of the support tube 3: a tube is extruded and cut to a fixed length to obtain the support tube 3;

Step A3. preparation of the elastic filter membrane 4: winding and weaving, and cutting a certain material to a fixed length to obtain the elastic filter membrane 4;

Step A4. preparation of the push catheter 1: a tube is extruded and cut to a fixed length to obtain the push catheter 1;

Step A5. preparation of the guide catheter 5: a tube is extruded and cut to a fixed length to obtain the guide catheter 5;

Step A6. preparation of the handle 6: the handle 6 is obtained by reverse injection molding and assembly process;

Step A7. the distal end of the plaque scraping stent 2 is welded to the distal end of the support tube 3; the elastic filter membrane 4 is bonded to an inner wall surface of the distal stent 23 of the plaque scraping stent 2; the proximal end of the plaque scraping stent 2 is welded to the distal end of the push catheter 1; the proximal end of the guide catheter 5 is bonded to the distal end of the handle 6, and the proximal end of the support tube 3 is bonded to the screw 65.

The above descriptions are only the preferred embodiments of the invention, not thus limiting the embodiments and scope of the invention. Those skilled in the art should be able to realize that the schemes obtained from the content of specification and drawings of the invention are within the scope of the invention.

What is claimed is:

1. A plaque removal device, comprising,
a push catheter (1), a plaque scraping stent (2), a support tube (3), an elastic filter membrane (4), a guide catheter (5), and a handle (6), wherein the plaque scraping stent (2) is a mesh structure sleeved outside the support tube (3), a distal end of the plaque scraping stent (2) is fixed on a distal end of the support tube (3), a proximal end of the plaque scraping stent (2) is fixed on a distal end of the push catheter (1), the support tube (3) is sleeved inside the push catheter (1), and a distance between the distal end of the push catheter (1) and the distal end of the support tube (3) is adjusted by the handle (6), so as to control an outer diameter of the plaque scraping stent (2) to be varied; wherein a surface of the plaque scraping stent (2) is provided with sharp edges for providing effective cutting; position of the plaque scraping stent (2) is changed by pushing, pulling, and rotating the handle (6), thereby cutting the plaque, resulting plaque fragments are collected in the elastic filter membrane (4) provided in the plaque scraping stent (2);
wherein the handle (6) comprises a luer taper (61), a safety lock (62), a slider device (63), a spring pressing cover (64), a screw (65) and an upper and lower front handle (66);
wherein an inner surface of the upper and lower front handle (66) is bonded to the proximal end of the guide catheter (5);
the proximal end of the support tube (3) passes through the guide catheter (5) and is fixedly connected to an inner surface of the screw (65); the slider device (63) is in thread connection with an outer surface of the screw (65), the slider device (63) is rotated to drive the screw (65) to move axially, and thus to drive the support tube (3), the plaque scraping stent (2) and the push catheter (1) to move axially;
the proximal end of the push catheter (1) passes through the guide catheter (5) into the handle (6), so as to be contact with a distal end of the screw (65); when the plaque scraping stent (2) moves to fully expose from the guide catheter (5), the proximal end of the push catheter (1) is in fixed coordination with the spring pressing cover (64), by pushing the spring pressing cover (64), the push catheter (1) moves axially with respect to the support tube (3) to change the outer diameter of the plaque scraping stent (2).

2. The plaque removal device of claim 1, wherein the plaque removal device (2) comprises a proximal stent (21), a lumbar stent (22) and a distal stent (23); wherein the proximal stent (21) and the distal stent (23) have a conical net structure, each of the proximal stent (21) and the distal stent (23) comprises 3-6 wide support rods (211), wherein the wide support rods (211) are distributed in a central symmetry manner, two thin support rods (212) extend from the wide support rods (211), 12, 16, 20 or 24 connection points are formed at junctions of the thin support rods (212) and the lumbar stent (22); the lumbar stent (22) has a tubular net structure, and comprises 12-24 diamond-shaped lumbar grids.

3. The plaque removal device of claim 1, wherein when the distance between the distal end of the push catheter (1) and the distal end of the support tube (3) is less than a farthest distance, that is, when the plaque scraping stent (2) is in an expanded state, an angle between two adjacent wide support rods (211) is a first opening angle $\angle 1$, wherein the first opening angle is in a range of 5° to 20°; an angle between two adjacent thin support rods (212) is a second opening angle $\angle 2$, wherein the second opening angle is in a range of 20° to 50°; an angle of the lumbar grids is a third opening angle $\angle 3$, wherein the third opening angle is in a range of 20° to 50°.

4. The plaque removal device of claim 1, wherein the plaque scraping stent (2) is an integral part which is carved from a nitinol tube, wherein the nitinol tube has an outer diameter of 1.4 mm and a length of 10 mm to 50 mm.

5. The plaque removal device of claim 1, wherein the elastic filter membrane (4) covers an inner wall of the distal stent (23), and is fixed by stitching, bonding or welding.

6. The plaque removal device of claim 1, wherein the elastic filter membrane (4) is made of PET or ePTFE material, the elastic filter membrane (4) is formed by cross weaving or sinusoidal weaving, wherein the elastic filter membrane (4) has a mesh size of 50 μm to 250 μm, and has a thickness of 10 μm to 200 μm.

7. The plaque removal device of claim 1, wherein the push catheter (1) is made of metal, non-metal or metal-non-metal composite tube with good flexibility and strong support.

\* \* \* \* \*